(12) United States Patent
Galivan et al.

(10) Patent No.: US 6,573,077 B1
(45) Date of Patent: *Jun. 3, 2003

(54) ACTIVE SITE OF HUMAN GAMMA GLUTAMYL HYDROLASE

(75) Inventors: John H. Galivan, Albany, NY (US); Thomas J. Ryan, Schenectady, NY (US); Ivan E. Auger, Castleton, NY (US)

(73) Assignee: Health Research Incorporated, Rensselaer, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/326,157

(22) Filed: Jun. 4, 1999

Related U.S. Application Data

(60) Continuation-in-part of application No. 09/128,722, filed on Aug. 4, 1998, now Pat. No. 5,962,235, which is a division of application No. 08/628,291, filed on Apr. 5, 1996, now Pat. No. 5,801,031.

(51) Int. Cl.[7] .................................................. C12N 15/57
(52) U.S. Cl. ................. 435/226; 435/320.1; 435/252.3; 435/476; 536/23.2
(58) Field of Search ................................ 435/195, 212, 435/226, 320.1, 252.3, 476, 490

(56) References Cited

U.S. PATENT DOCUMENTS

| | | | |
|---|---|---|---|
| 5,801,031 A | 9/1998 | Galivan et al. | 435/172.3 |
| 5,962,235 A | 10/1999 | Galivan et al. | 435/7.1 |

FOREIGN PATENT DOCUMENTS

| | | |
|---|---|---|
| WO | WO 95/14772 | 1/1995 |

OTHER PUBLICATIONS

Chave, K.J., et al. (2000) J. Biol. Chem. 275(51), 40365–40370.*
Acc. #T26504 (1995), n–gene seq. database.
Acc. #N45706 (1996), R77701 (1995), N53343 (1996), HO9442 (1995), and N48195 (1996), EST database (Hillier et al).
Barrueco et al., J Biol Chem 267:15356–15361 (1992).
Chandler et al., Am J Physiol 260:G865–G872 (1991).
Elsenhans et al., J Biol Chem 259:6364–6368 (1984).
Esaki et al., Gene 219:37–44 (1998).
Israeli et al., Cancer Research 53:227–230 (1993).
Leek et al., Br J Cancer 72(3):583–588 (1995).
McGuire and Coward, in "Folates and Pterins: vol. 1 Chemistry and Biochemistry of Folates", Blakely and Benkovic, eds., John Wiley & Sons, Inc., New York, pp. 135–190 (1984).
O'Connor et al., Cancer Research 51:3874–3881 (1991).
Pinto et al., Clinical Cancer Research 2(9):1445–1451 (1996).
Rao and Norohna, Biochim Biophys Acta 481:594–607 (1977).
Reisenauer et al., Science 198:196–197 (1977).
Rhee et al., Mol Pharmacol 53:1040–1046 (1998).
Saini and Rosenberg, J Biol Chem 249:5131–5134 (1974).
Silink et al., J Biol Chem 250:5982–5994 (1975).
Silver et al., Clinical Cancer Research 3:81–85 (1997).
Wang et al., Biochim Biophys Acta 1164:227–235 (1993).
Yao et al., Mol Pharmacol 48:505–511 (1995).
Yao et al., J Biol Chem 271:8525–8528 (1996.
Yato et al., Proc Natl Acad Sci USA 93:10134–10138 (1996).

* cited by examiner

Primary Examiner—Charles L. Patterson, Jr.
(74) Attorney, Agent, or Firm—Braman & Rogalskyj, LLP

(57) ABSTRACT

Provided is the active site of human gamma glutamyl hydrolase. The active site resides in amino acid residues 110, 171, 220 and 222 of SEQ ID NO:1. Thus provided is an inactive gamma glutamyl hydrolase protein, as well as a fragment thereof. A method of inactivating a gamma glutamyl hydrolase protein is also provided, as is a molecule capable of binding to one or more of amino acid residues 110, 171, 220 or 222 of SEQ ID NO:1 which can be used in such a method. A method for identifying a molecule that inactivates gamma glutamyl hydrolase is provided, as is a nucleic acid molecule encoding the inactive gamma glutamyl hydrolase.

14 Claims, 4 Drawing Sheets

SEQUENCE LISTING

<160> NUMBER OF SEQ ID NOS: 16

<210> SEQ ID NO 1
<211> LENGTH: 294
<212> TYPE: PRT
<213> ORGANISM: Homo sapiens

<400> SEQUENCE: 1

```
Arg Pro His Gly Asp Thr Ala Lys Lys Pro Ile Ile Gly Ile Leu Met
  1               5                  10                  15

Gln Lys Cys Arg Asn Lys Val Met Lys Asn Tyr Gly Arg Tyr Tyr Ile
             20                  25                  30

Ala Ala Ser Tyr Val Lys Tyr Leu Glu Ser Ala Gly Ala Arg Val Val
         35                  40                  45

Pro Val Arg Leu Asp Leu Thr Glu Lys Asp Tyr Glu Ile Leu Phe Lys
 50                  55                  60

Ser Ile Asn Gly Ile Leu Phe Pro Gly Gly Ser Val Asp Leu Arg Arg
 65                  70                  75                  80

Ser Asp Tyr Ala Lys Val Ala Lys Ile Phe Tyr Asn Leu Ser Ile Gln
             85                  90                  95

Ser Phe Asp Asp Gly Asp Tyr Phe Pro Val Trp Gly Thr Cys Leu Gly
            100                 105                 110

Phe Glu Glu Leu Ser Leu Leu Ile Ser Gly Glu Cys Leu Leu Thr Ala
            115                 120                 125

Thr Asp Thr Val Asp Val Ala Met Pro Leu Asn Phe Thr Gly Gly Gln
130                 135                 140

Leu His Ser Arg Met Phe Gln Asn Phe Pro Thr Glu Leu Leu Leu Ser
145                 150                 155                 160

Leu Ala Val Glu Pro Leu Thr Ala Asn Phe His Lys Trp Ser Leu Ser
            165                 170                 175

Val Lys Asn Phe Thr Met Asn Glu Lys Leu Lys Lys Phe Phe Asn Val
            180                 185                 190

Leu Thr Thr Asn Thr Asp Gly Lys Ile Glu Phe Ile Ser Thr Met Glu
            195                 200                 205

Gly Tyr Lys Tyr Pro Val Tyr Gly Val Gln Trp His Pro Glu Lys Ala
            210                 215                 220

Pro Tyr Glu Trp Lys Asn Leu Asp Gly Ile Ser His Ala Pro Asn Ala
225                 230                 235                 240

Val Asn Pro Ala Phe Tyr Leu Ala Glu Phe Val Asn Glu Ala Arg
            245                 250                 255

Lys Lys Asn His His Phe Lys Ser Glu Ser Glu Glu Lys Ala Leu
            260                 265                 270

Ile Tyr Gln Phe Ser Pro Ile Tyr Thr Gly Asn Ile Ser Ser Phe Gln
            275                 280                 285

Gln Cys Tyr Ile Phe Asp
    290
```

<210> SEQ ID NO 2
<211> LENGTH: 885
<212> TYPE: DNA

<213> ORGANISM: Homo sapiens

<400> SEQUENCE: 2

```
agacccacg gcgacaccgc caagaagccc atcatcggaa tattaatgca aaaatgccgt     60
aataaagtca tgaaaaacta tggaagatac tatattgctg cgtcctatgt aaagtacttg    120
gagtctgcag gtgcgagagt tgtaccagta aggctggatc ttacagagaa agactatgaa   180
atacttttca atctattaa tggaatcctt ttccctggag gaagtgttga cctcagacgc    240
tcagattatg ctaaagtggc caaaatattt tataacttgt ccatacagag ttttgatgat   300
ggagactatt ttcctgtgtg gggcacatgc cttggatttg aagagctttc actgctgatt   360
agtggagagt gcttattaac tgccacagat actgttgacg tggcaatgcc gctgaacttc   420
actggaggtc aattgcacag cagaatgttc cagaattttc ctactgagtt gttgctgtca   480
ttagcagtag aacctctgac tgccaatttc cataagtgga gcctctccgt gaagaatttt   540
acaatgaatg aaaagttaaa gaagtttttc aatgtcttaa ctacaaatac agatggcaag   600
attgagttta tttcaacaat ggaaggatat aagtatccag tatatggtgt ccagtggcat   660
ccagagaaag cacctatga gtggaagaat ttggatggca tttcccatgc acctaatgct   720
gtgaaccccg cattttattt agcagagttt tttgttaatg aagctcggaa aaagaaccat   780
cattttaaat ctgaatctga agaggagaaa gcattgattg atcagttcag tccaatttat   840
actggaaata tttcttcatt tcagcaatgt tacatatttg attga                  885
```

<210> SEQ ID NO 3
<211> LENGTH: 43
<212> TYPE: DNA
<213> ORGANISM: Homo sapiens

<400> SEQUENCE: 3

```
gcccatcatc ggaatattaa tgcaaaaagc ccgtaataaa gtc                      43
```

<210> SEQ ID NO 4
<211> LENGTH: 43
<212> TYPE: DNA
<213> ORGANISM: Homo sapiens

<400> SEQUENCE: 4

```
gactttatta cgggcttttt gcattaatat tccgatgatg ggc                      43
```

<210> SEQ ID NO 5
<211> LENGTH: 34
<212> TYPE: DNA
<213> ORGANISM: Homo sapiens

<400> SEQUENCE: 5

```
cctgtgtggg gcacagcgct tggatttgaa gagc                                34
```

<210> SEQ ID NO 6
<211> LENGTH: 34
<212> TYPE: DNA
<213> ORGANISM: Homo sapiens

<400> SEQUENCE: 6

```
gctcttcaaa tccaagcgct gtgccccaca cagg                                34
```

<210> SEQ ID NO 7
<211> LENGTH: 35
<212> TYPE: DNA
<213> ORGANISM: Homo sapiens

-continued

```
<400> SEQUENCE: 7
gctgattagt ggagaggcct tattaactgc cacag                              35

<210> SEQ ID NO 8
<211> LENGTH: 35
<212> TYPE: DNA
<213> ORGANISM: Homo sapiens

<400> SEQUENCE: 8
ctgtggcagt taataaggcc tctccactaa tcagc                              35

<210> SEQ ID NO 9
<211> LENGTH: 37
<212> TYPE: DNA
<213> ORGANISM: Homo sapiens

<400> SEQUENCE: 9
cttcatttca gcaagcttac atatttgatt gaaagtc                            37

<210> SEQ ID NO 10
<211> LENGTH: 37
<212> TYPE: DNA
<213> ORGANISM: Homo sapiens

<400> SEQUENCE: 10
gactttcaat caaatatgta agcttgctga aatgaag                            37

<210> SEQ ID NO 11
<211> LENGTH: 6
<212> TYPE: PRT
<213> ORGANISM: Homo sapiens

<400> SEQUENCE: 11

Met Gln Lys Cys Arg Asn
  1               5

<210> SEQ ID NO 12
<211> LENGTH: 16
<212> TYPE: PRT
<213> ORGANISM: Homo sapiens

<400> SEQUENCE: 12

Tyr Phe Pro Val Trp Gly Thr Cys Leu Gly Phe Glu Glu Leu Ser Leu
  1               5                  10                  15

<210> SEQ ID NO 13
<211> LENGTH: 6
<212> TYPE: PRT
<213> ORGANISM: Mus musculus

<400> SEQUENCE: 13

Met Gln Glu Cys Phe Gly
  1               5

<210> SEQ ID NO 14
<211> LENGTH: 16
<212> TYPE: PRT
<213> ORGANISM: Mus musculus

<400> SEQUENCE: 14

His Phe Pro Val Trp Gly Thr Cys Leu Gly Phe Glu Glu Leu Ser Val
  1               5                  10                  15
```

```
<210> SEQ ID NO 15
<211> LENGTH: 6
<212> TYPE: PRT
<213> ORGANISM: Rattus norvegicus

<400> SEQUENCE: 15

Met Gln Glu Cys Tyr Gly
 1               5

<210> SEQ ID NO 16
<211> LENGTH: 16
<212> TYPE: PRT
<213> ORGANISM: Rattus norvegicus

<400> SEQUENCE: 16

His Phe Pro Val Trp Gly Thr Cys Leu Gly Leu Glu Glu Leu Ser Val
 1               5                  10                  15
```

US 6,573,077 B1

ACTIVE SITE OF HUMAN GAMMA GLUTAMYL HYDROLASE

This application is a continuation-in-part of U.S. Ser. No. 09/128,722, filed Aug. 4, 1998, now U.S. Pat. No. 5,962,235 which was a divisional of U.S. Ser. No. 08/628,291, filed Apr. 5, 1996, now U.S. Pat. No. 5,801,031.

This invention was made with support from the United States Government under Grant No. CA 25933 of the National Cancer Institute, National Institutes of Health. The U.S. Government may have certain rights in this invention.

FIELD OF THE INVENTION

The subject invention is directed generally to gamma glutamyl hydrolase, and more particularly to the identification of the active site within gamma glutamyl hydrolase.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Many enzymes involved in producing precursors for DNA synthesis require folate as a cofactor. Antifolate drugs which impair folate function, such as methotrexate (MTX), are the primary treatments for many cancers. The retention and efficacy of folates and antifolate drugs within the cell are dependent on the addition of a poly-γ-glutamate chain to the monoglutamate (McBurney and Whitmore 1974). Folylpolyglutamate synthetase (FPGS) catalyzes the sequential addition of glutamate (for reviews see McGuire and Coward 1984; Shane 1989) and γ-glutamyl hydrolase (GH, EC 3.4.19.9) catalyzes the removal of glutamate from folyl- and antifolylpoly-γ-glutamates (for review see Galivan and Ryan 1998). In conjunction with the folate transport systems, the balance between GH and FPGS activity regulates the amount of glutamylation of folate and antifolate drugs in the cell.

GH activity in mammalian cells is found in the lysosomes (McGuire and Coward 1984; Hoffbrand and Peters 1969; Silink and Rowe 1975a; Wang et al. 1986; Yao et al. 1995). However, in cell culture, the major part of the synthesized enzyme is secreted into the medium (O'Connor et al. 1991). In humans, GH activity has been detected in plasma (Baggott et al. 1987), bile (Horne et al. 1981), pancreatic juice (Bhandari et al. 1990), and jejunal mucosa (Reisenauer et al. 1977). The enzyme has been purified from a number of mammalian tissues (Saini and Rosenberg 1974; Silink et al. 1975b; Rao and Norohna 1977; Elsenhans et al. 1984; Wang et al. 1993) and cell lines (Yao et al. 1995; O'Connor et al. 1991; Wang et al. 1993; Rhee et al. 1998). Both rat GH and human GH are glycoproteins (Rhee et al. 1998; Yao et al. 1996a). GH from different species has a different specificity in the hydrolysis of the poly-γ-glutamyl tail. For example, the rat GH enzyme acts as an endopeptidase (Wang et al. 1993) hydrolyzing the innermost γ-glutamyl bond and releasing the poly-γ-glutamate chain as a single unit. Conversely GH isolated from human sources (hGH) removes only the carboxyl terminal glutamate or di-γ-glutamate during the reaction (Rhee et al. 1998).

The cDNA's encoding GH from rat and human sources have been isolated (Yao et al. 1996a; Yao et al. 1996b; U.S. Pat. No. 5,801,031, issued Sep. 1, 1998 and incorporated herein by reference) and a mouse GH cDNA has recently been isolated (Esaki et al. 1998). The hGH CDNA has been expressed in both an insect expression system (Rhee et al. 1998) and *Escherichia coli* (Yao et al. 1996b). The first 24 amino acids encoded by the hGH cDNA are a signal peptide, which is removed during processing (Rhee et al. 1998). Therefore, the N-terminal amino acid of the mature hGH enzyme is equivalent to R25 in the published hGH sequence (Yao et al. 1996b).

Early studies demonstrated that GH is sulfhydryl sensitive and is inhibited by iodoacetic acid or p-hydroxymercuribenzoate (pHMB) (McGuire and Coward 1984; Reisenauer et al. 1977; Silink et al. 1975b). Studies on GH in lysosomes isolated from murine S180 cells indicate that accumulation of reduced sulfhydryls in the lysosome activate GH (Barrueco et al. 1992). Recent studies with pure GH preparations verified the earlier findings of sulfhydryl sensitivity (O'Connor et al. 1991; Rhee et al. 1998; Yao et al. 1996a).

The catalytic mechanism of GH has yet to be defined. A better understanding of the mechanism could lead to the specific inhibition of this enzyme and increased efficacy of antifolate drugs.

SUMMARY OF THE INVENTION

The subject invention addresses this need by identifying the active site of GH as including amino acid residues 110, 171, 220 and 222 of SEQ ID NO:1. SEQ ID NO:1 represents the amino acid sequence of mature human native GH (without the signal peptide). The subject invention thus provides an inactive gamma glutamyl hydrolase protein, the inactive protein having an amino acid sequence that substantially corresponds to the amino acid sequence of native gamma glutamyl hydrolase as shown in SEQ ID NO:1, SEQ ID NO:1 being modified at one or more of amino acid residues 110, 171, 220 or 222 to render the resulting gamma glutamyl hydrolase protein inactive. The invention further provides a fragment of the inactive gamma glutamyl hydrolase protein, wherein the fragment is from about 10 to about 150 amino acids in length and wherein the fragment includes one or more of the modified amino acid residues.

Also provided by the subject invention is a method of inactivating a gamma glutamyl hydrolase protein. The method comprises: providing a gamma glutamyl hydrolase protein; and modifying one or more of amino acid residues 110, 171, 220 or 222 in the amino acid sequence of the gamma glutamyl hydrolase protein as shown in SEQ ID NO:1, thereby inactivating the gamma glutamyl hydrolase protein.

Further provided is a molecule capable of binding to one or more of amino acid residues 110, 171, 220 or 222 in the amino acid sequence of gamma glutamyl hydrolase as shown in SEQ ID NO:1, wherein the molecule inactivates gamma glutamyl hydrolase and wherein the molecule has a three dimensional structure complementary to the three dimensional structure of gamma glutamyl hydrolase in a fragment that includes one or more of the amino acid residues 110, 171, 220 or 222. Compositions comprising the molecule and a suitable carrier, and the molecule and an antifolate, are also provided. The molecule can be used with an antifolate to increase the effectiveness of antifolate treatment.

The molecule can also be used to inactivate gamma glutamyl hydrolase protein. Such a method comprises: providing a gamma glutamyl hydrolase protein; and exposing the gamma glutamyl hydrolase protein to the above-described molecule, wherein the molecule binds to one or more of amino acid residues 110, 171, 220 or 222 in the amino acid sequence of the gamma glutamyl hydrolase protein thereby inactivating the gamma glutamyl hydrolase protein.

Further provided is a method of identifying a molecule that inactivates gamma glutamyl hydrolase protein. The method comprises: determining whether a molecule binds to one or more of amino acid residues 110, 171, 220 or 222 in the amino acid sequence of gamma glutamyl hydrolase as shown in SEQ ID NO:1; and screening a molecule that binds to one or more of amino acid residues 110, 171, 220 or 222 to determine whether the screened molecule inactivates gamma glutamyl hydrolase protein. A molecule identified by the method, as well as a method of inactivating gamma glutamyl hydrolase using the identified molecule, are also provided.

Further provided is a nucleic acid molecule encoding an inactive gamma glutamyl hydrolase protein, the nucleic acid molecule encoding an amino acid sequence that substantially corresponds to the amino acid sequence of native gamma glutamyl hydrolase as shown in SEQ ID NO:1, SEQ ID NO:1 being modified at one or more of amino acid residues 110, 171, 220 or 222 to render the resulting gamma glutamyl hydrolase protein inactive.

BRIEF DESCRIPTION OF THE DRAWINGS

These and other features and advantages of this invention will be evident from the following detailed description of preferred embodiments when read in conjunction with the accompanying drawings in which:

FIG. 1A shows a silver stained gel, and FIG. 1B shows a Western blot using a polyclonal antibody (1 to 10,000 dilution) against hGH expressed in insect cells. 1=wildtype, 2=C19A, 3=C110A, 4=C124A, 5=C290A;

DETAILED DESCRIPTION OF THE INVENTION

Figure 1A:
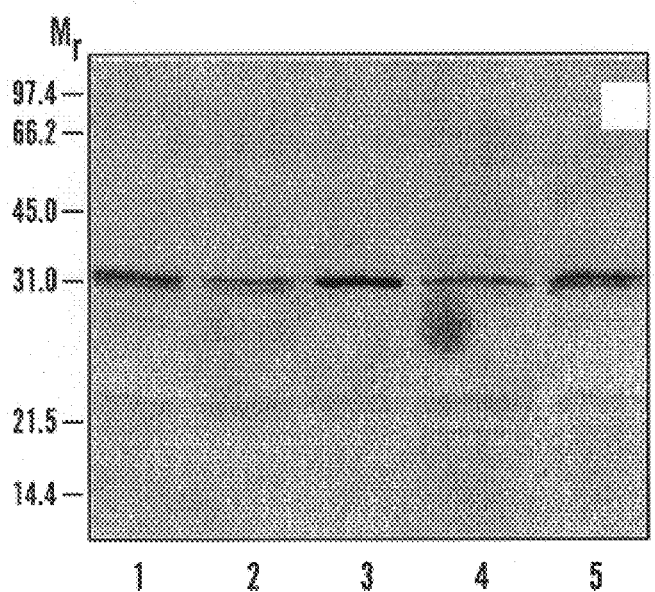
FIGS. 1A and 1B illustrate SDS 12.5% polyacrylamide gel electrophoresis of purified wildtype and mutant hGH proteins (0.58 $\mu$g per well).

The cDNA's encoding GH from rat and human sources have been isolated (Yao et al. 1996a; Yao et al. 1996b; U.S. Pat. No. 5,801,031, issued Sep. 1, 1998 and incorporated herein by reference). The hGH cDNA has been expressed in both an insect expression system (Rhee et al. 1998) and *Escherichia coli* (Yao et al. 1996b). The first 24 amino acids encoded by the hGH cDNA are a signal peptide, which is removed during processing (Rhee et al. 1998). Therefore, the N-terminal amino acid of the mature hGH enzyme is equivalent to R25 in the published hGH sequence (Yao et al. 1996b). As used herein, native gamma glutamyl hydrolase refers to mature human gamma glutamyl hydrolase protein as described in U.S. Pat. No. 5,801,031, issued Sep. 1, 1998. The mature protein could be in vivo or in vitro, and could be isolated from natural sources or synthesized using protein synthesis technology, including recombinant technology. The amino acid sequence of native gamma glutamyl hydrolase is shown in SEQ ID NO:1. The cDNA encoding native gamma glutamyl hydrolase is shown in SEQ ID NO:2. As discussed above, each of SEQ ID NO:1 and SEQ ID NO:2 have the signal peptide removed.

The subject invention provides an inactive gamma glutamyl hydrolase protein, the inactive protein having an amino acid sequence that substantially corresponds to the amino acid sequence of native gamma glutamyl hydrolase as shown in SEQ ID NO:1, SEQ ID NO:1 being modified at one or more of amino acid residues 110, 171, 220 or 222 to render the resulting gamma glutamyl hydrolase protein inactive. Further provided is a nucleic acid molecule encoding the inactive gamma glutamyl hydrolase protein.

As used herein, modified refers to a gamma glutamyl hydrolase protein having reduced catalytic activity in the removal of glutamate from folyl- and antifolylpoly-γ-glutamates when compared to the same catalytic activity of a gamma glutamyl hydrolase protein having an amino acid sequence as shown in SEQ ID NO:1. Modified refers to elimination of all catalytic activity (inactive), as well as less than 100% elimination of catalytic activity (such as a 50% or more reduction in catalytic activity).

The term "nucleic acid", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA, and nonfunctional DNA or RNA.

"Isolated" nucleic acid refers to nucleic acid which has been separated from an organism in a substantially purified form (i.e. substantially free of other substances originating from that organism), and to synthetic or recombinantly produced nucleic acid.

The phrase "nucleic acid molecule encoding" refers to a nucleic acid molecule which directs the expression of a specific protein. The nucleic acid sequences include both the DNA strand sequence that is transcribed into RNA and the RNA sequence that is translated into protein. The "nucleic acid molecule encoding" includes both the full length nucleic acid sequences as well as non-full length sequences derived from the full length protein. It being further understood that the "nucleic acid molecule encoding" further includes degenerate codons of the sequence as well as sequences which may be introduced to provide codon preference in a specific host cell.

The term "located upstream" as used herein refers to linkage of a promoter upstream from a nucleic acid sequence such that the promoter mediates transcription of the nucleic acid sequence.

The term "vector", refers to viral expression systems, autonomous self-replicating circular DNA (plasmids), and includes both expression and nonexpression plasmids. Where a recombinant microorganism or cell is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or the vector may be incorporated within the host's genome.

The term "plasmid" refers to an autonomous circular DNA molecule capable of replication in a cell, and includes both the expression and nonexpression types. Where a recombinant microorganism or cell is described as hosting an "expression plasmid", this includes latent viral DNA integrated into the host chromosome(s). Where a plasmid is being maintained by a host cell, the plasmid is either being stably replicated by the cell during mitosis as an autonomous structure, or the plasmid is incorporated within the host's genome.

The following terms are used to describe the sequence relationships between two or more nucleic acid molecules or polynucleotides, or between two or more amino acid sequences of peptides or proteins: "reference sequence", "comparison window", "sequence identity", "sequence homology", "percentage of sequence identity", "percentage of sequence homology", "substantial identity", and "substantial homology". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted, for example, by the local homology algorithm of Smith and Waterman (1981), by the homology alignment algorithm of Needleman and Wunsch (1970), by the search for similarity method of Pearson and Lipman (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to nucleic acid molecules or polynucleotides or nucleic acid sequences, the term "substantially corresponds to" includes "substantial identity", "substantial sequence identity", "substantial homology", and "substantial sequence homology".

As applied to nucleic acid molecules or polynucleotides, the terms "substantial identity" or "substantial sequence identity" mean that two nucleic acid sequences, when optimally aligned (see above), share at least 90 percent sequence identity, preferably at least 95 percent sequence identity, more preferably at least 96, 97, 98 or 99 percent sequence identity.

"Percentage nucleotide (or nucleic acid) identity" or "percentage nucleotide (or nucleic acid) sequence identity" refers to a comparison of the nucleotides of two nucleic acid molecules which, when optimally aligned, have approximately the designated percentage of the same nucleotides. For example, "95% nucleotide identity" refers to a comparison of the nucleotides of two nucleic acid molecules which when optimally aligned have 95% nucleotide identity. Preferably, nucleotide positions which are not identical differ by redundant nucleotide substitutions (the nucleotide substitution does not change the amino acid encoded by the particular codon).

As further applied to nucleic acid molecules or polynucleotides, the terms "substantial homology" or "substantial sequence homology" mean that two nucleic acid sequences, when optimally aligned (see above), share at least 90 percent sequence homology, preferably at least 95 percent sequence homology, more preferably at least 96, 97, 98 or 99 percent sequence homology.

"Percentage nucleotide (or nucleic acid) homology" or "percentage nucleotide (or nucleic acid) sequence homology" refers to a comparison of the nucleotides of two nucleic acid molecules which, when optimally aligned, have approximately the designated percentage of the same nucleotides or nucleotides which are not identical but differ by redundant nucleotide substitutions (the nucleotide substitution does not change the amino acid encoded by the particular codon). For example, "95% nucleotide homology" refers to a comparison of the nucleotides of two nucleic acid molecules which when optimally aligned have 95% nucleotide homology.

As applied to proteins or polypeptides or amino acid sequences, the term "substantially corresponds to" includes "substantial identity", "substantial sequence identity", "substantial homology", and "substantial sequence homology".

As applied to proteins or polypeptides, the terms "substantial identity" or "substantial sequence identity" mean that two protein or peptide sequences, when optimally aligned, such as by the programs GAP or BESTFIT using default gap, share at least 90 percent sequence identity, preferably at least 95 percent sequence identity, more preferably at least 96, 97, 98 or 99 percent sequence identity.

"Percentage amino acid identity" or "percentage amino acid sequence identity" refers to a comparison of the amino acids of two proteins or polypeptides which, when optimally aligned, have approximately the designated percentage of the same amino acids. For example, "95% amino acid identity" refers to a comparison of the amino acids of two proteins or polypeptides which when optimally aligned have 95% amino acid identity. Preferably, residue positions which are not identical differ by conservative amino acid substitutions. For example, the substitution of amino acids having similar chemical properties such as charge or polarity are not likely to affect the properties of a protein. Examples include glutamine for asparagine or glutamic acid for aspartic acid.

As further applied to proteins or polypeptides, the terms "substantial homology" or "substantial sequence homology" mean that two proteins or peptide sequences, when optimally aligned, such as by the programs GAP or BESTFIT using default gap, share at least 90 percent sequence homology, preferably at least 95 percent sequence homology, more preferably at least 96, 97, 98 or 99 percent sequence homology.

"Percentage amino acid homology" or "percentage amino acid sequence homology" refers to a comparison of the amino acids of two proteins or polypeptides which, when optimally aligned, have approximately the designated percentage of the same amino acids or conservatively substituted amino acids. For example, "95% amino acid homology" refers to a comparison of the amino acids of two proteins or polypeptides which when optimally aligned have 95% amino acid homology. As used herein, homology refers to identical amino acids or residue positions which are not identical but differ only by conservative amino acid substitutions. For example, the substitution of amino acids having similar chemical properties such as charge or polarity are not likely to affect the properties of a protein. Examples include glutamine for asparagine or glutamic acid for aspartic acid.

The phrase "substantially purified" or "isolated" when referring to a protein (or peptide), means a chemical composition which is essentially free of other cellular components. The protein or peptide can be separated from an organism or produced synthetically or recombinantly. It is preferably in a homogeneous state although it can be in either a dry or aqueous solution. Purity and homogeneity are typically determined using analytical chemistry techniques such as polyacrylamide gel electrophoresis or high performance liquid chromatography. A protein (or peptide) which is the predominant species present in a preparation is substantially purified. Generally, a substantially purified or isolated protein (or peptide) will comprise more than 80% of all macromolecular species present in the preparation. Preferably, the protein (or peptide) is purified to represent greater than 90% of all macromolecular species present. More preferably the protein (or peptide) is purified to greater than 95%, and most preferably the protein (or peptide) is purified to essential homogeneity, wherein other macromolecular species are not detected by conventional techniques.

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid sequence of the peptide or other protein to which the relevant sequence listing relates.

The DNA molecules and proteins of the subject invention also include those analogs, fragments or derivatives which differ from the inactive GH form in terms of the identity or location of one or more amino acid residues (deletion analogs containing less than all of the residues specified for the protein, substitution analogs wherein one or more residues specified are replaced by other residues, and addition analogs wherein one or more amino acid residues is added to a terminal or medial portion of the protein) and which share the catalytic activity (the reduction thereof) of the inactive GH. Such analogs, fragments or derivatives will include the modification at one or more of amino acid residues 110, 171, 220 or 222. At least one of these residues must be modified from the native form in the inactive form analog, fragment, or derivative. These molecules include, for example: the incorporation of codons "preferred" for expression by selected non-mammalian hosts (such as an N-terminal methionine residue); the provision of sites for cleavage by restriction endonuclease enzymes; and the provision of additional initial, terminal or intermediate DNA sequences that facilitate construction of readily expressed vectors.

As used herein, a "fragment" of the inactive gamma glutamyl hydrolase protein refers to an amino acid sequence of about 10 to about 150 amino acids. Preferably, the fragments are less than 50 amino acids in length, and more preferably the fragments are 10–20 amino acids in length or 20–40 amino acids in length. A fragment as used herein is specifically intended to include one or more of the modified amino acids residues (residues 110, 171, 220 or 222). Such a fragment is specifically provided by the subject invention.

The proteins and fragments thereof described herein can contain any naturally-occurring or non-naturally-occurring amino acids, including the D-form of the amino acids, amino acid derivatives and amino acid mimics, so long as the desired function and activity of the protein/fragment is maintained. The choice of including an (L)- or a (D)-amino acid in the protein/fragment of the present invention depends, in part, on the desired characteristics of the protein/fragment. For example, the incorporation of one or more (D)-amino acids can confer increased stability on a protein/fragment and can allow a protein/fragment to remain active in the body for an extended period of time. The incorporation of one or more (D)-amino acids can also increase or decrease the pharmacological activity of a protein/fragment.

The protein/fragment may also be cyclized, since cyclization may provide the protein/fragment of the present invention with superior properties over their linear counterparts.

As used herein, the terms "amino acid mimic" and "mimetic" mean an amino acid analog or non-amino acid moiety that has the same or similar functional characteristic of a given amino acid. For instance, an amino acid mimic of a hydrophobic amino acid is one which is non-polar and retains hydrophobicity, generally by way of containing an aliphatic chemical group. By way of further example, an arginine mimic can be an analog of arginine which contains a side chain having a positive charge at physiological pH, as is characteristic of the guanidinium side chain reactive group of arginine.

In addition, modifications to the peptide backbone and peptide bonds thereof are also encompassed within the scope of amino acid mimic or mimetic. Such modifications can be made to the amino acid, derivative thereof, non-amino acid moiety or the peptide either before or after the amino acid, derivative thereof or non-amino acid moiety is incorporated into the protein. What is critical is that such modifications mimic the peptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al. (1981) and Raucher et al. (1980). An amino acid mimic is, therefore, an organic molecule that retains the similar amino acid pharmacophore groups as are present in the corresponding amino acid and which exhibits substantially the same spatial arrangement between functional groups.

The substitution of amino acids by non-naturally occurring amino acids and amino acid mimics as described above can enhance the overall activity or properties of an individual protein/fragment thereof based on the modifications to the backbone or side chain functionalities. For example, these types of alterations can enhance the protein's/fragment's stability to enzymatic breakdown and increase biological activity. Modifications to the peptide backbone similarly can add stability and enhance activity.

One skilled in the art, using the above sequences or formulae, can easily synthesize the proteins/fragments of this invention. Standard procedures for preparing synthetic peptides are well known in the art. The novel peptides can be synthesized using: the solid phase peptide synthesis (SPPS) method of Merrifield (1964) or modifications of SPPS; or, the peptides can be synthesized using standard solution methods well known in the art (see, for example, Bodanzsky (1993)). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten (1985).

The inactive GH of the subject invention is inactivated by modifying one or more of amino acid residues 110, 171, 220 or 222 in SEQ ID NO:1. The one or more amino acid residues can be modified by any means known in the art. Site directed mutagenesis of a nucleic acid molecule which encodes the amino acid sequence can be used to substitute another amino acid for the native amino acid. Antibodies, small molecules, or short peptides could be used which bind to and block the residue (thereby interfering with the 3-dimensional conformation of the active protein). Both of these scenarios are intended to be included as a "modified" amino acid.

The invention thus further provides a method of inactivating gamma glutamyl hydrolase protein. The method comprises providing a gamma glutamyl hydrolase protein, and modifying one or more of amino acid residues 110, 171, 220 or 222 in the amino acid sequence of the gamma glutamyl hydrolase protein as shown in SEQ ID NO:1 (thereby inactivating the gamma glutamyl hydrolase protein).

Figure 3:
FIG. 3 illustrates the 3-dimensional conformation of gamma glutamyl hydrolase, showing the conformational relationship of amino acid residues 110, 171, 220 and 222.
Figure 4:
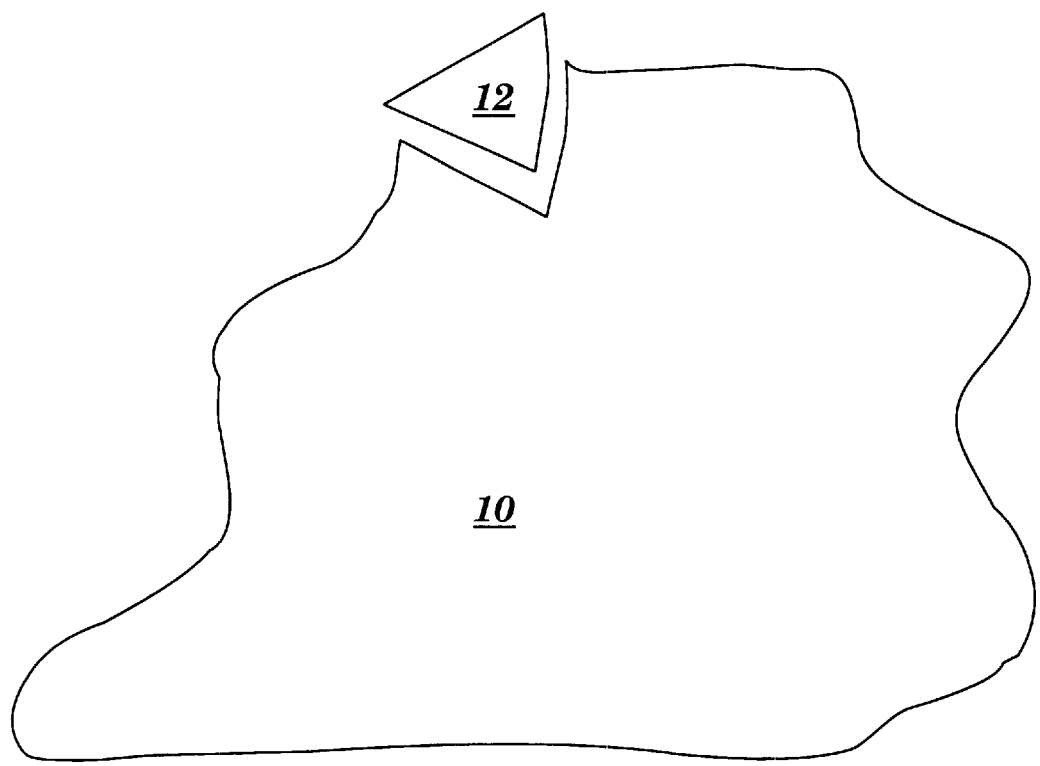
FIG. 4 illustrates the conformations of an antigen that is complementary to the three dimensional structure of an antibody.

A molecule capable of binding to one or more of amino acid residues 110, 171, 220 or 222 in the amino acid sequence of gamma glutamyl hydrolase as shown in SEQ ID NO:1 is also provided, wherein the molecule inactivates gamma glutamyl hydrolase and wherein the molecule has a three dimensional structure complementary to the three dimensional structure of gamma glutamyl hydrolase in a fragment that includes one or more of the one or more of amino acid residues 110, 171, 220 or 222. The three dimensional structure of gamma glutamyl hydrolase is shown in FIG. 3, including the location of residues 110, 171, 220, and 222. The concept of a complementary three dimensional structure is clearly illustrated in FIG. 4, which shows the conformations of an antigen (10) complementary to the three dimensional structure of an antibody (12).

As should be readily apparent to those skilled in the art, the isolated molecule could be, for example, an antibody (such as a polyclonal or monoclonal antibody, including chimeric or humanized antibodies), a peptide (of about 10 to about 100 amino acids in length, preferably less than 50 and most preferably 10–20 or 20–40 amino acids in length), or other small molecule capable of binding to one or more of amino acid residues 110, 171, 220 or 222. By "binding to" is meant covalent or non-covalent attachment to the particular amino acid residue or otherwise blocking of the particular amino acid residue. For example, amino acid residue 110 could be bound by an antibody that recognizes an epitope that includes amino acid residue 110. A small molecule which covalently attaches to amino acid residue 110 also "binds" that residue 110. Alternatively, a small molecule which covalently attaches to amino acid residues 109 and 111, effectively sterically blocking amino acid residue 110, is considered to "bind" amino acid residue 110 as used herein. Bind is therefore used in the broader sense of blockage of three dimensional conformation of the particular amino acid.

Suitable molecules capable of binding to one or more of amino acid residues 110, 171, 220 or 222 can be identified by any means known in the art. For example, a peptide can be synthesized which includes amino acid residues 105–115 of SEQ ID NO:1. The chemically synthesized peptide can be conjugated to bovine serum albumin and used for raising polyclonal antibodies in rabbits. Standard procedures can be used to immunize the rabbits and to collect serum, as described below. Polyclonal antibody can be tested for its ability to bind to GH (or the GH fragment 105–115). For polyclonal antibody that shows a high affinity binding to GH, functional studies can then be undertaken for reduction in GH catalytic activity. Fragments (such as Fab, Fc, F(ab')$_2$) of the polyclonal antibody can be made if steric hindrance appears to be preventing an accurate evaluation of more specific modulating effects of the antibody (Becker and Miller 1989, Kupinski and Miller 1986, and Miller et al. 1986). Polyclonal antibody to the synthetic peptide that recognizes GH and reduces GH catalytic activity can be obtained at ≧95% purity and conjugated to bovine serum albumin or to another carrier protein, for the production of murine monoclonal antibodies.

Alternatively, monoclonal antibody production can be carried out using BALB/c mice. Immunization of B-cell donor mice can involve immunizing them with antigens mixed in TiterMax™ adjuvant as follows: 50 μg antigen/20 μl emulsion×2 injections given by an intramuscular injection in each hind flank on day 1. Blood samples can be drawn by tail bleeds on days 28 and 56 to check the titers by ELISA assay. At peak titer (usually day 56) the mice can be subjected to euthanasia by $CO_2$ inhalation, after which splenectomies can be performed and spleen cells harvested for the preparation of hybridomas by standard methods.

Once a monoclonal antibody has been identified which binds to one or more of amino acid residues 110, 171, 220 or 222, bacteriophage display libraries can be used to identify peptide molecules which mimic the monoclonal antibody conformation. Such identified peptides can then be used in turn to identify peptide molecules that bind to the original amino acid residues 110, 171, 220 or 222 (the concept of mimetic compounds).

Scott and Smith (1990) presented a method of defining peptide ligands by using randomly synthesized peptide inserts in bacteriophage. Related methods were published by Cwirla et al. (1990) and by Devlin et al. (1990). Since that time a literature has arisen in which both the original hexapeptide inserts and larger inserts have been used in identifying epitopes recognized by monoclonal antibodies. For example, a well-balanced decapeptide (10-mer) library (described by Christian et al. 1992) or a dodecapeptide (12-mer) library (Clontech Laboratories, Palo Alto, Calif.) can be used. The strategy for using these libraries largely follows the review presented by Scott (1992) and employs, with modifications, the detailed methodology for use of this system as described by Smith and Scott (1993). A useful strategy is described below in the Materials and Methods.

Having thus identified molecules capable of binding to one or more of amino acid residues 110, 171, 220 or 222, tissues or cells could be contacted with compositions of the molecules in order to inactivate gamma glutamyl hydrolase and/or to increase the effectiveness of antifolate treatment. In the context of this invention, to "contact" tissues or cells with a composition means to add the composition, usually in a suitable liquid carrier, to a cell suspension or tissue sample, either in vitro or ex vivo, or to administer the composition to cells or tissues within an animal (including humans). In one embodiment, the composition may comprise the molecule and the anti-folate together as one composition (mixed or attached to one another by any means known in the art, including covalent or non-covalent attachment or other binding). By contacting the tissues or cells with the compositions of the molecules, the gamma glutamyl hydrolase protein present in the tissues or cells is thereby exposed to the molecule.

The formulation of therapeutic compositions and their subsequent administration is believed to be within the skill in the art. In general, for therapeutics, a patient suspected of needing such therapy is given a composition in accordance with the invention, commonly in a pharmaceutically acceptable carrier, in amounts and for periods which will vary depending upon the nature of the particular disease, its severity and the patient's overall condition. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

In addition to such pharmaceutical carriers, cationic lipids may be included in the formulation to facilitate uptake. One such composition shown to facilitate uptake is Lipofectin (BRL, Bethesda Md.).

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual compositions, and can generally be calculated based on $IC_{50}$'s or $EC_{50}$'s in in vitro and in vivo animal studies. For example, given the molecular weight of compound and an effective dose such as an $IC_{50}$, for example (derived experimentally), a dose in mg/kg is routinely calculated.

The subject invention thus also provides a method of inactivating gamma glutamyl hydrolase protein. The method comprises providing a gamma glutamyl hydrolase protein, and exposing the gamma glutamyl hydrolase protein to the molecule described above. The molecule binds to one or more of amino acid residues 110, 171, 220 or 222 in the amino acid sequence of the gamma glutamyl hydrolase protein, thereby inactivating the gamma glutamyl hydrolase protein.

As indicated above, the molecules according to the subject invention are particularly useful to increase the effectiveness of antifolate treatment. Such a method is provided by the subject invention, and comprises co-administering the molecule and an antifolate. Co-administering is intended to cover simultaneous (as one combined or as two simultaneously administered separate compositions) or sequential administration of the molecule and the antifolate separately.

As used herein, "antifolate" refers to antifolates which are converted to polyglutamates (specifically, antifolylpolyglutamates) in host or tumor tissues. Examples of antifolates as used herein include, for example, methotrexate, aminopterin, and more recently developed antifolates such as edetrexate, lomotrexol, BW1843U89, and ZD1694 (Fleming and Schilsky 1992; Bertino 1993). The resulting antifolylpolyglutamates are then degraded by gamma glutamyl hydrolase back to the parent compound (the antifolate) and glutamic acid. In general, the antifolylpolyglutamates are more toxic due to their greater cellular retention and tighter binding to a drug target than the antifolates.

The invention also provides a method of identifying a molecule that inactivates gamma glutamyl hydrolase protein. The method comprises determining whether a molecule binds to one or more of amino acid residues 110, 171, 220 or 222 in the amino acid sequence of gamma glutamyl hydrolase as shown in SEQ ID NO:1, and screening a molecule that binds to one or more of amino acid residues 110, 171, 220 or 222 to determine whether the screened molecule inactivates gamma glutamyl hydrolase protein. Examples of such a method are described in further detail above in the context of identification of antibody or peptide molecules which bind to one or more of amino acid residues 110, 171, 220 or 222.

If the molecule is a peptide, phage display libraries can be used to determine whether the molecule binds to the peptide fragment which includes the amino acid residue. If the molecule is an antibody, the antibody can be immobilized on a solid support and the peptide fragment which includes the amino acid residue can be labeled with a detectable marker and contacted with the immobilized antibody. After washing, the presence of the label will indicate that the antibody bound to the peptide. Likewise, the peptide could be immobilized and the antibody could be contacted with the immobilized peptide. These techniques are readily known in the art.

Once a suitable molecule has been identified, which molecule is also provided by the subject invention, the molecule can be used to inactivate gamma glutamyl hydrolase protein or to increase the effectiveness of antifolate treatment.

The subject invention also provides a nucleic acid molecule encoding an inactive gamma glutamyl hydrolase protein, the nucleic acid molecule encoding an amino acid sequence that substantially corresponds to the amino acid sequence of native gamma glutamyl hydrolase as shown in SEQ ID NO:1, SEQ ID NO:1 being modified at one or more of amino acid residues 110, 171, 220 or 222 to render the resulting gamma glutamyl hydrolase protein inactive. Preferably, the nucleic acid molecule has a nucleic acid sequence that substantially corresponds to the nucleic acid sequence of native gamma glutamyl hydrolase protein as shown in SEQ ID NO:2, SEQ ID NO:2 being modified at one or more of nucleotides 328–330, 511–513, 658–660, or 664–666 (the nucleotides which encode amino acid residues 110, 171, 220, and 222, respectively).

The nucleic acid molecule can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the inactivated GH.

The nucleic acid molecules of the subject invention can be expressed in suitable host cells using conventional techniques. Any suitable host and/or vector system can be used to express the inactive GH. Bacterial hosts (for example, Escherichia coli) and mammalian hosts (for example, Hela cells, Cv-1 cells, COS cells) are preferred. In tumor host cells, where the hydrolysis effect of GH on antifolylpolyglutamates decreases the efficiency of the antifolate treatment, it is desirable to decrease or prevent expression of native GH. Thus, tumor cells are a particularly suitable host in which to decrease native GH expression such as by expression of the inactive GH of the subject invention instead of native GH.

Techniques for introducing the nucleic acid molecules into host cells may involve the use of expression vectors which comprise the nucleic acid molecules. These expression vectors (such as plasmids and viruses; viruses including bacteriophage) can then be used to introduce the nucleic acid molecules into suitable host cells. For example, DNA encoding the inactive GH can be injected into the nucleus of a host cell or transformed into the host cell using a suitable vector, or mRNA encoding the inactive GH can be injected directly into the host cell, in order to obtain expression of inactive GH in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures. DNA can also be incorporated into artificial lipid vesicles, liposomes, which fuse with the cell membrane, delivering their contents directly into the cytoplasm. In an even more direct approach, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

Further methods for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. For a review of baculovirus vectors, see Miller (1989). Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

With this understanding of the scope of the subject invention, the details which follow describe the identification of the catalytic (active) site of human gamma glutamyl hydrolase (GH), as well we the elucidation of the 3-dimensional structure of GH in the region (fragment) that includes the catalytic site. Specifically, using site-directed mutagenesis the cDNA for human GH was altered to encode four different proteins each with one of four cysteine residues changed to alanine. Three of the mutant proteins had activities similar to wildtype GH and were inhibited by iodoacetic acid whereas the C110A mutant had no activity. C110 is conserved among the human, rat and mouse GH amino acid sequences. The wildtype protein and all four mutants had similar intrinsic fluorescence spectra indicating no major structural changes had been introduced. These results indicate that C110 is catalytically essential and suggest that GH is a cysteine peptidase.

Using sensitive sequence analysis methods to extract subtle patterns from sequence databases, a statistical significance similarity was found between human gamma glutamyl hydrolase (hGH) and the class-I glutamine amidotransferase family of enzymes. In particular, the catalytic active site from the latter is conserved in hGH as well as other amino acids near the catalytic residues. This leads to the conclusion that hGH folds similar to the class-I glutamine amidotransferases. Referring to FIG. 3, the 3-dimensional model predicts that Cys110 functions as the active site nucleophile attacking the γ-carbonyl of glutamine to form a glutamyl thioester intermediate (Thoden et al. 1998). The model also predicts that His 220 and Glu 222 in hGH are the other two amino acids in the catalytic triad. His 220 and Glu 222 are conserved in the human, rat and mouse glutamyl hydrolase sequences. In the proposed model for hGH, His 220 would activate Cys 110 and Glu 222 would stabilize the resulting positively charged imidizolium cation. The alignment model also predicts that His 171 points away from the catalytic triad and is involved in substrate binding not catalysis.

Materials and Methods

Construction of C19A, C10A, C124A, and C290A Mutants of hGH

A cDNA encoding the 294 amino acid mature form of hGH protein with an N-terminal methionine preceding the first arginine residue had previously been subcloned into pET-24a (pET-hGH, Yao et al. 1996b) (Novagen, Madison, Wis.). Site-directed mutagenesis was performed with the QuickChange kit (Stratagene, La Jolla, Calif.) according to the manufacturer's protocol using 125 ng of each primer for the C110A mutation and 150 ng for the other mutations, and annealing temperatures of 55° C. for C110A and 53° C. for the other mutations. The oligonucleotides synthesized for the mutagenesis were as follows, (codon changed is underlined and mismatched basepairs are in bold).

GHC19+ (SEQ ID NO:3) 5'-GCC CAT CAT CGG AAT ATT AAT GCA AAA A<u>GC</u> <u>C</u>G TAA TAA AGT C-3'
GHC19−(SEQ ID NO:4) 5'-GAC TTT ATT ACG <u>GGC</u> TTT TTG CAT TAA TAT TCC GAT GAT GGG C-3'
GHC110+ (SEQ ID NO:5) 5'-CCT GTG TGG GGC ACA <u>GCG</u> CTT GGA TTT GAA GAG C-3'
GHC110−(SEQ ID NO:6) 5'-GCT CTT CAA ATC CAA <u>GCG</u> <u>C</u>TG TGC CCC ACA CAG G-3'
GHC124+ (SEQ ID NO:7) 5'-GCT GAT TAG TGG AGA G<u>GC</u> <u>C</u>TT ATT AAC TGC CAC AG-3'
GHC124−(SEQ ID NO:8) 5'-CTG TGG CAG TTA ATA <u>AGG</u> <u>C</u>CT CTC CAC TAA TCA GC-3'
GHC290+ (SEQ ID NO:9) 5'-CTT CAT TTC AGC AA<u>G</u> <u>C</u>TT ACA TAT TTG ATT GAA AGT C-3'
GHC290−(SEQ ID NO:10) 5'-GAC TTT CAA TCA AAT ATG TA<u>A</u> <u>GCT</u> TGC TGA AAT GAA G-3'

Plasmid DNA was purified using the Plasmid Midi kit (Qiagen, Santa Clarita, Calif.). The sequences of all mutant clones were confirmed using automated DNA sequencing on either an Applied Biosystems 373A or 377A DNA sequencer (Perkin Elmer, Branchburg, N.J.)

Expression and Purification of Wildtype and Mutant hGH

Mutant plasmids were used to transform *E. coli* strain BL21(DE3)pLysS to kanamycin resistance. Cultures (20 ml) were grown for 16 hours at 37° C., 225 rpm in tryptone-phosphate broth (Moore et al. 1993), containing 30 μg/ml kanamycin and 34 μg/ml chloramphenicol. An aliquot (6 ml) of this culture was used to inoculate 500 ml of the same medium. Cultures were incubated at 27° C., 225 rpm until the $OD_{600nm}$ was 0.5–0.6. Isopropyl β-D-thiogalactoside (IPTG) was added to a final concentration of 1 mM and cultures were incubated for a further 3 hours.

Cells were harvested by centrifugation and stored at −80° C. Cells from 1 liter of broth were resuspended in 50 ml of 50 mM Tris/HCl pH 7.5 buffer containing 500 mM NaCl and Complete protease inhibitor cocktail (Boehringer Mannheim, Indianapolis, Ind.). The mixture was sonicated and clarified by centrifugation at 20,000 g for 30 minutes at 4° C. A 20–60% ammonium sulfate precipitate was resuspended in 50 mM sodium acetate, pH 5.8, 1 mM octyl-β-D-glucoside (OBG) and 5% glycerol (buffer A). After dialysis at 4° C. against buffer A and clarification by centrifugation at 30,000 g, 4° C. for 120 minutes, the dialysate was applied in two aliquots to a Protein Pak SP columnn (1.0 cm×10 cm, Waters Division of Millipore Corp., Milford, Mass.) equilibrated in buffer A. The protein was eluted (1 ml/min) with a linear gradient in buffer A of 0 to 1M NaCl over 60 minutes. Fractions were assayed for hGH activity or for hGH protein by Western blot. Fractions containing hGH were pooled and frozen at −80° C. Wildtype hGH and the C19A, C110A, and C290A mutants eluted as two peaks whereas the C124A mutant eluted as a single peak coincident with the first peak for the other hGH proteins. Western blotting analysis indicated that the hGH in both peaks was of the same Mr. There was 8–10 times more hGH protein in peak 1 than in peak 2. A statistically significant amount (40–82%) of enzyme activity of proteins purified on the SP column was lost when stored either at 4° C. or at −80° C. Thawed aliquots of peak 1 were incubated for 2 hours at 4° C. with 2 ml of pHMB agarose (0.8 μmole/ml agarose) (Sigma Chemical, St. Louis, Mo.) equilibrated in 50 mM sodium acetate pH 5.8, 20 mM OBG, 500 mM NaCl (buffer B). The matrix was poured into a column (0.75 cm×4.5 cm) and washed with buffer B. hGH protein was eluted with buffer B containing additionally 10 m dithiothreitol and 50 mM β-mercaptoethanol. EDTA (1 mM final) was added to each fraction to inhibit remaining proteases. Fractions containing hGH were pooled and stored at −80° C.

Protein Concentration Assay

Protein concentrations were determined using the Coomassie Plus protein assay reagent (Pierce, Rockford, Ill.) with bovine serum albumin as the standard. The concentrations of purified wildtype and mutant hGH proteins were normalized according to the intensity of their intrinsic fluorescence spectra relative to the spectra of C110A (the most pure protein).

Activity Assays hGH activity in chromatography fractions was measured with $4-NH_2-10-CH_3PteGlu_5$ (Schirk Labs, Jona, Switzerland) as previously described (Rhee et al. 1998). The specific activities and reaction kinetics of hGH were determined using varying concentrations of $4-NH_2-10-CH_3PteGlu_2$ as substrate (Schirk Labs). $K_m$ and $V_{max}$ were determined by the method of Hanes (Price and Stevens 1989) with the best fit line calculated using Excel (Microsoft). Iodoacetate inhibition was performed as previously described using 0.5 mM iodoacetate for 60 minutes (Rhee et al. 1998).

SDS-PAGE

Proteins were separated using 12% (4% stacking) SDS-PAGE gels. Protein bands were visualized by silver staining (Bio-Rad, Hercules, Calif.), following the manufacturer's protocol.

Western Blotting hGH protein was determined by Western blotting as previously described (Rhee et al. 1998).

Measurement of Intrinsic Fluorescence

Intrinsic fluorescence of wildtype and mutant hGH proteins was measured on a Perkin Elmer LS-50B fluorescence spectrometer.

Biopanning of Monoclonal Antibody with Bacteriophage Display Libraries

In the first round of biopanning a 60 mm streptavidin-coated petri dish is filled with blocking solution (0.5% BSA, 0.1 M $NaHCO_3$, 0.1 μg/ml streptavidin, 0.2% $NaN_3$) for 2 hours, then washed three times with TBS-0.5% Tween. Next, 1 μl of the library (about $1 \times 10^{11}$ phage) that has been incubated overnight at 4° C. with 1 μg of biotinylated Mab is diluted with 1 ml of TBS-Tween, and this mixture is then added to the petri dish and rocked for 15 minutes at room temperature. The petri dish is washed 10 times with TBS-Tween, and bound phage is eluted by pipetting 800 μl of 0.1 N HCl (pH adjusted to 2.2 with glycine)–1 mg/ml BSA into the dish. The eluate is then pipetted into a microfuge tube containing 48 μl of 2M Tris, to bring the pH up to about 8.

The eluate is concentrated and washed twice in TBS using an Amicon Centricon-30 filter (Amicon, Inc., Beverly, Mass.). This final product is titered out by making dilutions from a small amount of concentrated eluate in TBS-0.1% gelatin and adding 1 μl of each dilution made to 19 μl of TBS-gelatin, then adding 20 μl of starved K91 *E. coli* cells and incubating for 10 minutes at room temperature. After adding 200 μl of NZY medium containing 0.2 μg/ml tetracycline (Tc) and incubating at 37° C. for 1 hour, the mixture is plated out on NZY agar plates containing 40 μg/ml tetracycline and allowed to grow up overnight at 37° C.

After titering, the entire concentrated eluate from the first round of biopanning (about 50 μl) is added to an equal volume of fresh starved K91 cells, and amplification performed as described by Smith and Scott (1993). Following the first PEG/NaCl precipitation, the resulting pellet is dissolved in 1 ml TBS. Phage is then precipitated a second time with PEG/NaCl, allowed to stand at least 1 hour at 4° C., and the precipitate collected following centrifugation at 4° C. After careful removal of all the supernatant, the pellet is dissolved in 100 μl TBS. This amplified product can then be titered.

The second biopanning also uses 1 μg of biotinylated antibody with $1 \times 10^{11}$ phage, and the second round of biopanning is concentrated and amplified as in the first round. In the third round, 0.01 μg of biotinylated antibody is biopanned against $2.5 \times 10^{11}$ phage. The third round is stopped after eluting the bound phage from the petri dish. This eluate is not concentrated or amplified. Titerings are done before and after each round, and the percent yield is calculated as the number of bacteriophage obtained in an elution fraction relative to the initial number of bacteriophage (Christian et al. 1992). A yield should generally be greater than $10^{-5}$ to exceed background, with values of $10^{-4}$ to $10^{-1}$ typically observed. Increasing percent yields in subsequent rounds of biopanning are, in particular, suggestive that clones of increasing affinity are being selected.

In some experiments, an immunological screening assay, as described by Christian, et al. (1992) may be performed using NZY+Tc agar plates containing about 500 well-separated colonies. The colonies are transferred to nitrocellulose membrane filters (Biorad Laboratories, Hercules, Calif.), and the filters are immediately washed twice in TNT Buffer (10 mM Tris, pH 8.0, 150 mM NaCl, 0.05% Tween 20), blocked for 30 minutes at room temperature with gentle agitation in 20% normal goat serum in TNT buffer, then incubated for 2 hours at room temperature in primary mab that has been diluted 1:1000 in blocking buffer. The filters are washed sequentially for 10 minutes at room temperature each wash, in washing buffer A (TNT Buffer+0.1% BSA), washing buffer B (TNT Buffer+0.1% BSA+0.1% NP-40), and then again washing buffer A, and incubated in a secondary peroxidase-conjugated goat anti-mouse IgG for 1½ hours at room temperature. The filters are washed as before, then put in a final wash of TN (10 mM Tris, pH. 7.5, 150 mM NaCl). Color development is observed after putting filters in ABTS substrate.

Small cultures of individual colonies are then grown up overnight, by either: a) selecting the colonies that were positive from the immunological screening; or b) skipping the screening step and randomly selecting colonies (about 100). Each colony is inoculated into 2 ml of NZY medium containing 20 µg/ml tetracycline, and these small cultures grown up overnight at 37° C., with vigorous shaking. The next day cultures are centrifuged to pellet the cells, and the supernatant is removed. To 1 ml of the supernatant is then added 150 µl PEG/NaCl, and the phage are precipitated overnight at 4° C. Following subsequent centrifugation and removal of supernatant, the pellet is dissolved in 1 ml TBS.

For DNA sequencing, 400 µl of the dissolved pellet is extracted once with phenol, and the resulting aqueous phase (about 300 µl) is added to 500 µl TE and 80 µl 3M sodium acetate buffer. Then 1 ml ethanol is added and the SS DNA is allowed to precipitate overnight at 4° C. Each sample is then microfuged for 30 minutes at 4° C., the DNA pellet washed once in 70% ETOH, dried, and resuspended in 7 µl $H_2O$. This template can be stored at −20° C. until ready to use.

Due to the quite GC-rich Sfi I cloning site flanking the insertion region (Christian et al. 1992), sequencing reactions are carried out using the Sequenase 7-deaza dGTP DNA sequencing kit (Amersham-US Biochemicals, Arlington Heights, Ill.) with $^{32}P$-dATP and an antisense primer located approximately 40 nucleotides 3' to the insert site. Samples are run on a standard 6% sequencing gel using an IBI STS 45 sequencing apparatus (Eastman Kodak Company, Rochester, N.Y.). The GCG software (Genetics Computer Group, Inc., Madison Wis.) is helpful for aligning sequences obtained from multiple clones in order to find consensus sequences.

EXAMPLE I
Expression and Purification of Wildtype and Mutant hGH Proteins

Site-directed mutagenesis was used to generate C19A, C110A, C124A, and C290A variants of hGH, each having 1 cysteine codon replaced by an alanine codon. Wildtype and mutant proteins were expressed in *Escherichia coli* using the pET expression system (Studier and Moffatt 1986). Wildtype hGH and the C19A, C110A, C124A, and C290A mutants were initially purified on a SP cation exchange column. In the case of the C110A mutant no fractions contained hGH activity.

Figure 1B:
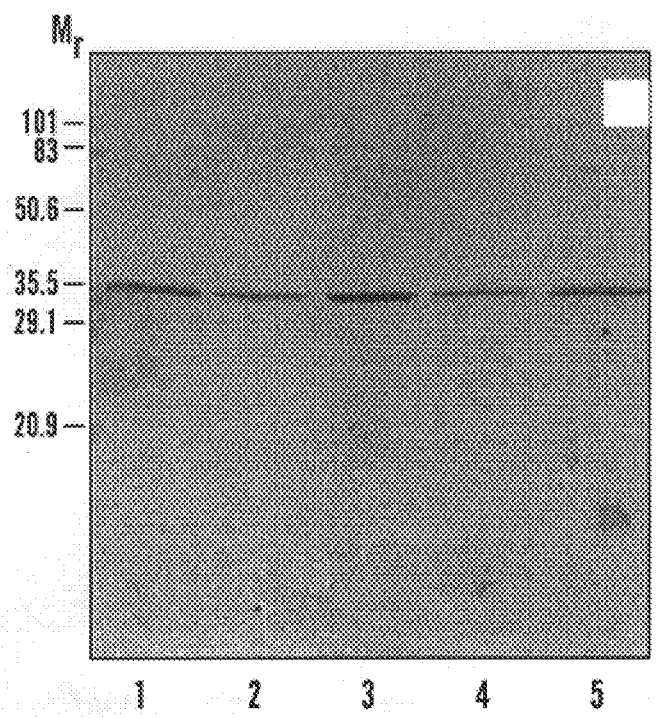

The SP purified proteins were further purified on a column of pHMB linked to agarose (Waltham et al. 1997). All four cysteine mutant proteins bound to pHMB coupled agarose indicating that there was more than one cysteine residue in hGH, which bound this matrix. Using this procedure wildtype hGH was isolated with an overall yield of 11%. Analysis by SDS-PAGE and Western blotting of pooled fractions indicated hGH was purified to near homogeneity (FIG. 1). The Mr of the major band at 35 kDa is in agreement with the theoretical mass of the cDNA encoded protein (Yao et al. 1996b). In most preparations there was a minor non-immunoreactive protein that copurified with hGH and had a fractionally lower Mr.

EXAMPLE II
Activity of Wildtype and Mutant hGH Proteins

The specific activities of the purified hGH proteins are summarized in Table 1. Wildtype, C19A, C124A, and C290A hGH proteins had activity and all produced a similar product distribution of methotrexate polyglutamates when 4-$NH_2$-10-$CH_3PteGlu_5$ was used as a substrate. The specific activities of C19A and C124A were significantly lower than for the wildtype protein but these proteins had a higher amount of contaminating protein (FIG. 1). The activities of wildtype, C19A, C124A, and C290A proteins were reduced 70–94% by incubation with 0.5 mM iodoacetate for 60 minutes. The fact that the C19A, C124A and C290A mutant proteins were inhibited by iodoacetate suggests that all these mutant proteins still contain a catalytically essential cysteine residue, namely C110.

The $K_m$ and $V_{max}$ for the active hGH proteins with 4-$NH_2$-10-$CH_3PteGlu_2$ were determined (Table 1). The $V_{max}$ values for the wildtype and active mutants were not significantly different, indicating that the differences in specific activities of the purified proteins (Table 1) were due to an increased amount of contaminant protein. The Km values for 4-$NH_2$-10-$CH_3PteGlu_2$ with the C19A, C124A, and C290A mutant hGH proteins were significantly lower than for wildtype hGH, indicating a higher affinity for this substrate. The C110A mutant had no activity (less than 0.01% of wildtype enzyme) when assayed with either 4-$NH_2$-10-$CH_3PteGlu_2$ or the better substrate, 4-$NH_2$-10-$CH_3PteGlu_5$.

An amino acid sequence alignment of the human (Yao et al. 1996b), rat (Yao et al. 1996a) and mouse (Esaki et al. 1998) GH proteins indicated the C19 and C110 were invariant in all three sequences (Table 2). Since the C19A mutant had a $V_{max}$ similar to the wildtype hGH, C19 cannot be catalytically essential. There are no equivalents of C124 or C290 in rat or mouse GH proteins. Therefore, it is unlikely that either is involved in catalysis.

The C19A, C124A and C290A proteins all had increased affinities for 4-$NH_2$-10-$CH_3PteGlu_2$. Although hGH cleaves both at the carboxyl terminal and penultimate γ-glutamyl bond, the penultimate bond is favored (Rhee et al. 1998). It has also been demonstrated that 4-$NH_2$-10-$CH_3PteGlu_2$ is a poor substrate for hGH relative to longer chain polyglutamates (Rhee et al. 1998); Rhee et al. 1995), presumably because hydrolysis can occur only at the terminal γ-glutamyl bond. Therefore, the increased affinity for 4-$NH_2$-10-$CH_3PteGlu_2$ by the active mutants may be a feature of this particular substrate. Given the complex nature of cleavage of substrates with longer chain lengths, it is currently impossible to obtain detailed kinetic data for these more favored substrates. The similar product distribution shown when the active mutants were assayed with 4-$NH_2$-10-$CH_3PteGlu_5$, favoring cleavage at the penultimate γ linkage (Rhee et al. 1998) suggests that these mutations had no effect on the specificity of the location of the γ-bond cleavage.

The loss of activity when C110 is mutated to alanine and the fact that C110 is conserved in the amino acid sequences of human, rat and mouse GH indicates that this is the essential cysteine.

EXAMPLE III
Intrinsic Fluorescence of hGH and Mutant Proteins

Figure 2:
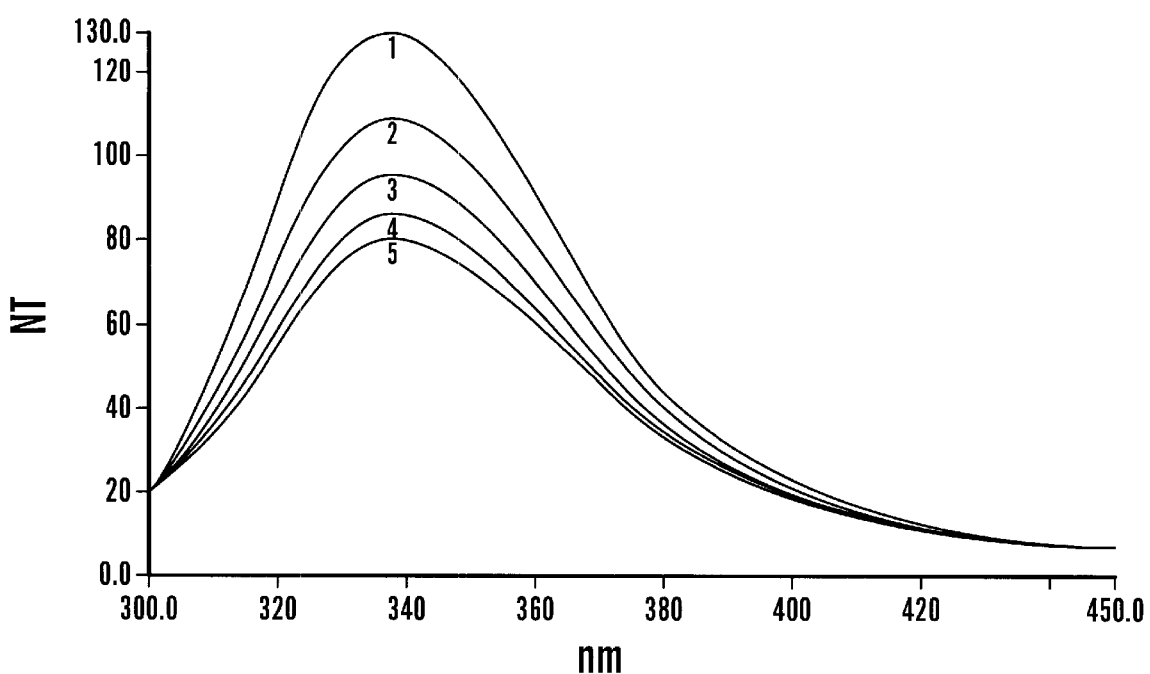
FIG. 2 illustrates intrinsic fluorescence spectra of wildtype and mutant hGH proteins (0.58 $\mu$g/ml in 50 mM sodium acetate pH 5.5, 50 mM β-mercaptoethanol, 1 mM octyl-β-glucoside). Excitation was at 280 nm. The spectra are numbered as follows: 1=C110A, 2=wildtype, 3=C290A, 4=C19A, 5=C124A.

Wildtype and mutant hGH proteins were diluted to the same concentration of total protein and the intrinsic fluorescence spectra of these proteins were measured. Excitation at 280 nm produced emission spectra that were identical in shape and $\lambda_{max}$ for all the purified hGH proteins (FIG. 2). The intrinsic fluorescence spectra were also identical to that measured for hGH expressed in insect cells. Differences in fluorescence intensity could be attributed to the slight differences in purity between the preparations as seen by silver stained SDS-PAGE and Western blotting (FIG. 1) and specific activities (Table 1). Emission spectra had a fluorescence intensity peak at 337–338 nm. Although this method cannot detect very small structural changes it suggests that there were no major structural changes caused by mutagenesis.

EXAMPLE IV
Three-dimensional Model for the Catalytic Site of Human Gamma Glutamyl Hydrolase Many enzymes involved in producing precursors for DNA synthesis require folate as a cofactor. Antifolate drugs, for example, methotrexate, which impair folate function, are the primary treatments for many cancers. The retention and efficacy of folates and antifolate drugs within the cell are dependent on the addition of a poly-γ-glutamate chain to the monoglutamate. Folylpolyglutamate synthetase (FPGS) catalyzes the sequential addition of glutamate and γ-glutamyl hydrolase (GH) catalyzes the removal of glutamate from folyl and antifolyl poly-γ-glutamates. The balance between GH and FPGS activity regulates the amount of glutamylation of folate and antifolate drugs in the cell. The use of low molecular weight inhibitors of GH in conjunction with conventional antifolates would be expected to increase the efficacy of the antifolate treatment.

Key to the design of low molecular weight inhibitors and mechanism based inhibitors of hGH is a knowledge of both the three dimensional structure of the active site and an identification of the catalytic mechanism including the catalytic amino acids. The three dimensional structure of hGH has not been determined. However a significant advance has been made in this regard. Using sensitive sequence analysis methods to extract subtle patterns from sequence databases, a statistical significance similarity was found between human gamma glutamyl hydrolase (hGH) and the class-I glutamine amidotransferase family of enzymes. In particular, the catalytic active site from the latter is conserved in hGH as well as other amino acids near the catalytic residues.

A two step process was used to generate the sequence similarity model. First, using the sequence of hGH as the query, a search of swissprot plus trembl databases was made using the program Ssearch (Pearson 1995) which uses the Smith-Waterman algorithm to identify statistically significant sequence similarities. The set of protein sequences obtained from this search was then used as a starting set for the TPROBE (Neuwald et al. 1997) program, which extracts protein alignment models from protein databases. Amongst the set of sequences that belong to the identified sequence alignment model are two that have a known high resolution X-ray structure. The similarity is with the glutamine amidotransferase domain of the small subunit of carbamoyl phosphate synthetase (CPS) from *E. coli* (Thoden et al. 1997), and with GMP synthetase (Tesmer et al. 1996). In particular, the catalytic triad Cys-His-Glu is strongly conserved in the sequence alignment model.

To illustrate the possible similarities, see FIG. 3 which is the proposed structure of gamma glutamyl hydrolase (and which is the structure of the small subunit of CPS) showing the regions identified by the protein alignment model. The continuous ribbon illustrates the region of human γ-glutamyl hydrolase aligned to CPS.

CPS contains two domains and catalyzes the synthesis of carbamoyl phosphate from bicarbonate, glutamine, and two molecules of MgATP. The smaller subunit is the site of glutamine hydrolysis to produce ammonia for deliver to the larger subunit. In agreement with the site directed mutagenesis study described above, the model predicts that Cys110 in hGH is analogous to Cys 269 in CPS, which functions as the active site nucleophile attacking the γ-carbonyl of glutamine to form a glutamyl thioester intermediate (Thoden et al. 1998). The model also predicts that His 220 and Glu 222 in hGH are the other two amino acids in the catalytic triad, corresponding to His 353 and Glu 355 in CPS. His 220 and Glu 222 are conserved in the human, rat and mouse glutamyl hydrolase sequences. In the proposed model for hGH, His 220 would activate Cys 110 and Glu 222 would stabilize the resulting positively charged imidizolium cation. Studies also show that mutating His 171 to Ala in an *E. coli* expression system inactivates hGH. Interestingly the alignment model predicts that His 171 is analogous to His 312 in CPS. His 312 in CPS points away from the catalytic triad and is involved in substrate binding not catalysis. When His 312 in CPS was conservatively mutated to Asn, the $K_M$ for the substrate was increased 200-fold (Miran et al. 1991). A similar or greater increase in substrate $K_M$ for the His 171A mutant of hGH might explain the lack of activity that was observed. Further reinforcing evidence for this alignment model was obtained by running the Pfam HMM search program (Sonnhammer et al. 1998). The Pfam result has an E-value of 0.13 with the GATase model of class-I glutamine amidotransferases. Although this is not statistically significant, the alignment is similar to the one obtained using TPROBE. The alignment of the catalytic triad Cys-His-Glu is also found using Pfam but this program does not identify the His 171 in hGH.

The proposed three-dimensional model for the active site of hGH is consistent with the overall chemistry being catalyzed, nucleophilic attack on the gamma carbonyl of a glutamic acid amide by an activated Cys to release either glutamic acid or di gamma-Glu.

This model for the active site of hGH has been tested by preparing the Cys110Ala, His220Ala, Glu222Ala, His171Ala, and His171Asn mutants of hGH. The mutants were expressed in the baculovirus system used for active hGH to facilitate the rapid expression and purification of the proteins. The mutant proteins were characterized for activity on methotrexate polyglutamates. Consistent with the predictions of the model that Cys110 and His220 are two amino acids of the catalytic triad, the mutants C110A and H220A were found to be inactive. The mutant Glu222Ala was active but had a greatly reduced activity relative to the wildtype enzyme. This is consistent with Glu222 being the third residue of the catalytic triad since when a similar mutation (Glu355Gly) was made in the model enzyme CPS, the mutant retained activity but it was greatly reduced (Hewagama et al. 1998). The role of His171 in hGH has been examined by preparing the mutant His171Ala and the more conservative mutation His171Asn. Both of these mutants were found to be inactive on methotrexate tetraglutamate suggesting that this residue in hGH plays a critical role either in binding substrate or maintaining the structure of the enzyme.

These studies establish hGH as a cysteine peptidase of the Cys-His-Glu catalytic triad class and indicate that the catalytic site of hGH folds in a fashion similar to CPS. The amino acids constituting the catalytic triad have been determined and His 171 is identified as a key residue in binding substrate or maintaining the structure of the enzyme.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

$K_m$, $V_{max}$ and specific activities of purified wildtype hGH and mutant hGH proteins

| Protein | $K_m$ (μM) | $V_{max}$ (nmol 4-$NH_2$-10-$CH_3PteGlu_2$ hydrolyzed/min/μg protein) | Specific activity (nmol 4-$NH_2$-10-$CH_3PteGlu_2$ hydrolyzed/min/mg protein) |
|---|---|---|---|
| Wildtype | 55.2 ± 8.4 | 2.7 ± 0.9 | 1913 ± 32 |
| C19A | 18.1 ± 0.4[a] | 1.1 ± 0.3 | 1000 ± 72[a] |
| C124A | 28.5 ± 3.7[a] | 1.0 ± 0.1 | 725 ± 79[a] |
| C290A | 19.5 ± 8.6[a] | 1.9 ± 0.4 | 1406 ± 463 |
| C110A | — | — | no activity |

[a]compared to wildtype, $p < 0.01$

Results are Mean±Standard Deviation of 3 Experiments $K_m$ and $V_{max}$ activities were measured using variable 4-$NH_2$-10-$CH_3PteGlu_2$ substrate concentrations. Specific activities were measured using 200 μM 4-$NH_2$-10-$CH_3PteGlu_2$ for 5 minutes.

TABLE 2

Alignment of known GH amino acid sequences between amino acids 16–21 and 103–118.

| | Amino acids[a] | |
|---|---|---|
| Species | 16–21 | 103–118 |
| Homo sapiens[b] | MQKCRN (SEQ ID NO:11) | YFPVWGTCLGFEELSL (SEQ ID NO:12) |
| Mus musculus[c] | MQECFG (SEQ ID NO:13) | HFPVWGTCLGFEELSV (SEQ ID NO:14) |
| Rattus norvegicus[d] | MQECYG (SEQ ID NO:15) | HFPVWGTCLGLEELSV (SEQ ID NO:16) |

[a]amino acids highlighted in bold are conserved in all three GH sequences; underlined are C19 and C110.
[b]Yao et al. 1996b
[c]Esaki et al. 1998
[d]Yao et al. 1996a

REFERENCES

Baggott, J. E., et al., Am J Clin Nutr 46:295–301 (1987).
Barrueco, J. R., et al., J Biol Chem 267:15356–15361 (1992).
Becker, B. H. and Miller, J. L., Blood 74:690–694 (1989).
Bertino, J. R., J Clin Oncol 11:5–14 (1993).
Bhandari, S. D., et al., J Nutr 120:467–475 (1990).
Bodanzsky, M., "Principles of Peptide Synthesis", 2d Ed., Springer-Verlag (1993).
Capecchi, M., Cell 22:479–488 (1980).
Christian, R. B., et al., J Mol Biol 227:711–718 (1992).
Cwirla, S. E., et al., Proc Natl Acad Sci USA 87:6378–6382 (1990).
Devlin, J. J. et al., Science 249:404–406 (1990).
Elsenhans, B., et al., J Biol Chem 259:6364–6368 (1984).
Esaki, T., et al., Gene 219:37–44 (1998).
Fleming, G. and Schilsky, R. L., Seminar in Oncology 19:707–719 (1992).
Galivan, J., and Ryan, T. J., in "Handbook of Proteolytic Enzymes", Barrett, A. J., et al., Eds., Academic Press, London, pp. 783–786 (1998).
Hewagama, A., et al., Biochim Biophys Acta 1388:489–499 (1998).
Hoffbrand, A. V., and Peters, T. J., Biochem Biophys Acta 192:479–485 (1969).
Horne, D. W., et al., J Nutr 111:442–449 (1981).
Houghten, Proc Natl Acad Sci USA 82:5131 (1985).
Kupinski, J. M. and Miller, J. L., Thromb Res 43:335–344 (1986).
Klein, T. M., et al., Nature 327:70–73 (1987).
Mannino, R. J. and Gould-Fogerite, S., BioTechniques 6:682–690 (1988).
McBurney, M. W., and Whitmore, G. F., Cell 2:173–182 (1974).
McGuire, J. J., and Coward, J. K., in "Folates and Pterins", vol. 1, Blakely, R. L., and Benkovic, S. J., Eds., John Wiley and Sons, New York, N.Y., pp. 135–190 (1984).
Merrifield, J Am Chem Soc 85:2149 (1964).
Miller, J. L. et al., Blood 68:743–751 (1986).
Miller, L. K., Bioessays 11:91–95 (1989).
Miran, S. G., et al., Biochemistry 30:7901–7907 (1991).
Moore, J. T., et al., Protein Expr Purif 4:160–163 (1993).
Needleman and Wunsch, J Mol Biol 48:443 (1970).
Neuwald, A. F., et al., Nucleic Acids Research 9:1665–1677 (1997).
O'Connor, B. M., et al., Cancer Res 51:3874–3881 (1991).
Pearson, W. R., Protein Sci 4:1145–1160 (1995).
Pearson and Lipman, Proc Natl Acad Sci USA 85:2444 (1988).
Price, N. C., and Stevens, L., "Fundamentals of Enzymology", $2^{nd}$ edition, Oxford University Press, Oxford (1989).
Rao, K. N., and Norohna, J. M., Biochim Biophys Acta 481:594–607 (1977).
Raucher et al., Tetrahedron Lett 21:14061 (1980).
Reisenauer, A. M., et al., Science 198:196–197 (1977).
Rhee, M. S., et al., Cell Pharmacol 2:289–292 (1995).
Rhee, M. S., et al., Mol Pharmacol 53:1040–1046 (1998).
Saini, P. K., and Rosenberg, I. H., J Biol Chem 249:5131–5134 (1974).
Sambrook et al., "Molecular Cloning: A Laboratory Manual", 2d Edition, Cold Spring Harbor Laboratory Press, Cold Spring Harbor, N.Y. (1989).
Scott, J. K., Trends in Biochem Sci 17:241–245 (1992).
Scott, J. K. and Smith, G. P., Science 249:386–390 (1990).
Shane, B., Vitam Horm 45:263–335 (1989).
Shigekawa, K. and Dower, W. J., BioTechniques 6:742–751 (1988).
Silink, M., and Rowe, P. B., Biochem Biophys Acta 381:28–36 (1975a)
Silink, M., et al., J Biol Chem 250:5982–5994 (1975b).
Smith, G. P. and Scott, J. K., Methods in Enzymology 217:228–257 (1993).
Smith and Waterman, Adv Appl Math 2:482 (1981).
Sonnhammer, E. L., et al., Nucleic Acids Research 26:320–322 (1998).
Studier, F. W., and Moffatt, B. A., J Mol Bibl 189:113–130 (1986).
Tesmer, J. J. G., et al., Nat Struct Biol 3:74–86 (1996).
Thoden, J. B., et al., Biochemistry 36:6305–6316 (1997).
Thoden, J. B., et al., Biochemistry 37:8825–8831 (1998).
Waltham, M. C., et al., Mol Pharmacol 51:825–832 (1997).

Wang, T. T. Y., et al., J Biol Chem 261:13551–13555 (1986).
Wang, Y., et al., Biochim Biophys Acta 1164:227–235 (1993).
Wann et al., JOC 46:257 (1981).
Yao, R., et al., Mol Pharmacol 48:505–511 (1995).
Yao, R., et al., J Biol Chem 271:8525–8528 (1996a).
Yao, R., et al., Proc Natl Acad Sci USA 93:10134–10138 (1996b).

What is claimed is:

1. A modified gamma glutamyl hydrolase protein having reduced catalytic activity in glutamate removal when compared to catalytic activity in glutamate removal of native gamma glutamyl hydrolase protein, the modified protein having the amino acid sequence of native gamma glutamyl hydrolase as shown in SEQ ID NO:1 modified at one or more of amino acid residues 110, 171, 220 or 222 to reduce the catalytic activity in glutamate removal of the resulting gamma glutamyl hydrolase protein.

2. The modified gamma glutamyl hydrolase protein of claim 1 wherein the one or more amino acid residues are modified by amino acid substitution.

3. The modified gamma glutamyl hydrolase protein of claim 1 wherein the one or more amino acid residues are modified by binding of a molecule thereto.

4. A fragment of the modified gamma glutamyl hydrolase protein of claim 1, wherein the fragment is from about 10 to about 150 amino acids in length and wherein the fragment includes one or more of the modified amino acid residues.

5. The fragment of claim 4 wherein the one or more amino acid residues are modified by amino acid substitution.

6. The fragment of claim 4 wherein the one or more amino acid residues are modified by binding of a molecule thereto.

7. A method of reducing catalytic activity in glutamate removal of a gamma glutamyl hydrolase protein when compared to catalytic activity in glutamate removal of native gamma glutamyl hydrolase protein, the method comprising:

providing a native gamma glutamyl hydrolase protein having an amino acid sequence as shown in SEQ ID NO:1; and modifying one or more of amino acid residues 110, 171, 220 or 222 in the amino acid sequence of the native gamma glutamyl hydrolase protein, thereby reducing the catalytic activity in glutamate removal of the gamma glutamyl hydrolase protein.

8. The method of claim 7 wherein the modifying comprises substitution of the one or more of amino acid residues 110, 171, 220 or 222.

9. The method of claim 7 wherein the modifying comprises binding of a molecule to the one or more of amino acid residues 110, 171, 220 or 222.

10. A nucleic acid molecule encoding a modified gamma glutamyl hydrolase protein having reduced catalytic activity in glutamate removal when compared to catalytic activity in glutamate removal of native gamma glutamyl hydrolase protein, the nucleic acid molecule encoding an amino acid sequence as shown in SEQ ID NO:1 modified at one or more of amino acid residues 110, 171, 220 or 222 to reduce the catalytic activity in glutamate removal of the resulting gamma glutamyl hydrolase protein.

11. The nucleic acid molecule of claim 10 having a nucleic acid sequence as shown in SEQ ID NO:2 modified at one or more of nucleotides 328–330, 511–513, 658–660, or 664–666.

12. A recombinant cell comprising the nucleic acid molecule of claim 10.

13. An expression vector comprising the nucleic acid molecule of claim 10.

14. A cell comprising the expression vector of claim 13.

* * * * *